United States Patent
Shiraki et al.

(10) Patent No.: US 11,744,440 B2
(45) Date of Patent: *Sep. 5, 2023

(54) INFORMATION PROCESSING APPARATUS, INFORMATION PROCESSING METHOD, AND ENDOSCOPE SYSTEM FOR PROCESSING IMAGES BASED ON SURGICAL SCENES

(71) Applicant: Sony Corporation, Tokyo (JP)

(72) Inventors: Hisakazu Shiraki, Kanagawa (JP); Masahito Yamane, Kanagawa (JP); Kenji Takahasi, Kanagawa (JP); Takeshi Uemori, Tokyo (JP); Kentaro Fukazawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 536 days.

This patent is subject to a terminal disclaimer.

(21) Appl. No.: 16/929,693

(22) Filed: Jul. 15, 2020

(65) Prior Publication Data

US 2020/0345220 A1 Nov. 5, 2020

Related U.S. Application Data

(63) Continuation of application No. 15/761,438, filed as application No. PCT/JP2016/080496 on Oct. 14, 2016, now Pat. No. 10,722,106.

(30) Foreign Application Priority Data

Oct. 30, 2015 (JP) ................................. 2015-213767

(51) Int. Cl.
*A61B 1/045* (2006.01)
*G06K 9/00* (2022.01)
(Continued)

(52) U.S. Cl.
CPC .......... *A61B 1/000095* (2022.02); *A61B 1/00* (2013.01); *A61B 1/045* (2013.01);
(Continued)

(58) Field of Classification Search
CPC .. A61B 1/00; A61B 1/04; A61B 1/045; G06K 9/00711; G06T 3/4053;
(Continued)

(56) References Cited

U.S. PATENT DOCUMENTS

2007/0013771 A1* 1/2007 Imaizumi ............... A61B 1/043
348/76
2008/0074649 A1* 3/2008 Levenson ............. G06F 18/251
356/73

(Continued)

FOREIGN PATENT DOCUMENTS

CN 1838730 A1 9/2006
CN 102151117 A1 8/2011
(Continued)

OTHER PUBLICATIONS

International Search Report dated Dec. 27, 2017 in PCT/JP2016/060496.

*Primary Examiner* — James T Boylan
(74) *Attorney, Agent, or Firm* — XSENSUS LLP

(57) ABSTRACT

An information processing apparatus, an information processing method, and an endoscope system capable of providing an optimal video image to an operator in accordance with surgical scenes are provided. A processing mode determination unit determines, in accordance with surgical scenes, a processing mode for an in-vivo image captured by an imaging apparatus including an imaging element arranged so as to enable pixel shift processing, and an image combining unit processes an image output from the imaging apparatus, in accordance with the processing mode. The (Continued)

| SURGICAL SCENES | PROCESSING MODES |
|---|---|
| NBI AND FLUORESCENCE OBSERVATION | HIGH DEFINITION MODE AND NR MODE |
| SUTURING | HIGH DEFINITION MODE |
| SCOPE MOVEMENT | HFR MODE |
| CAREFUL STRIPPING | HIGH DEFINITION MODE |
| NORMAL STRIPPING | HFR MODE |
| OTHER SCENES | NORMAL MODE | present technology is applicable to, for example, an endoscope system for imaging a living body with an endoscope.

13 Claims, 12 Drawing Sheets

(51) Int. Cl.
| | |
|---|---|
| *G06T 3/40* | (2006.01) |
| *G06T 5/00* | (2006.01) |
| *H04N 5/225* | (2006.01) |
| *H04N 5/232* | (2006.01) |
| *A61B 1/00* | (2006.01) |
| *G06V 20/40* | (2022.01) |
| *H04N 23/56* | (2023.01) |
| *H04N 23/667* | (2023.01) |
| *H04N 23/50* | (2023.01) |

(52) U.S. Cl.
CPC ............ *G06T 3/4053* (2013.01); *G06T 5/002* (2013.01); *G06V 20/40* (2022.01); *H04N 23/56* (2023.01); *H04N 23/667* (2023.01); *H04N 23/555* (2023.01)

(58) Field of Classification Search
CPC ............ G06T 5/002; H04N 2005/2255; H04N 5/2256; H04N 5/23245
See application file for complete search history.

(56) References Cited

U.S. PATENT DOCUMENTS

| | | |
|---|---|---|
| 2009/0240108 A1 | 9/2009 | Shimizu et al. |
| 2012/0092472 A1 | 4/2012 | Higuchi |
| 2014/0100427 A1 | 4/2014 | Saito et al. |
| 2014/0125828 A1 | 5/2014 | Takeuchi |
| 2015/0105758 A1* | 4/2015 | Igarashi ............... A61B 1/0638 606/3 |
| 2016/0088267 A1* | 3/2016 | Niijima ................. H04N 23/88 348/237 |
| 2016/0360125 A1 | 12/2016 | Yamamoto et al. |
| 2018/0033142 A1* | 2/2018 | Morita ................ A61B 5/7203 |
| 2018/0279853 A1 | 10/2018 | Daidoji et al. |

FOREIGN PATENT DOCUMENTS

| | | |
|---|---|---|
| EP | 2772182 A1 | 9/2014 |
| JP | 2005-305046 A | 11/2005 |
| JP | 2009-225933 A | 10/2009 |
| JP | 2010-268244 A | 11/2010 |
| JP | 2011-95073 A | 5/2011 |
| WO | 2015/125553 A1 | 8/2015 |
| WO | 2016/162925 A1 | 10/2016 |
| WO | 2017/051455 A1 | 3/2017 |

* cited by examiner

FIG. 4

| SURGICAL SCENES | PROCESSING MODES |
|---|---|
| NBI AND FLUORESCENCE OBSERVATION | HIGH DEFINITION MODE AND NR MODE |
| SUTURING | HIGH DEFINITION MODE |
| SCOPE MOVEMENT | HFR MODE |
| CAREFUL STRIPPING | HIGH DEFINITION MODE |
| NORMAL STRIPPING | HFR MODE |
| OTHER SCENES | NORMAL MODE |

FIG. 6

| SURGICAL SCENES | PROCESSING MODES |
|---|---|
| NBI AND FLUORESCENCE OBSERVATION | HIGH DEFINITION MODE |
| SUTURING | HIGH DEFINITION MODE |
| SCOPE MOVEMENT | HFR MODE |
| CAREFUL STRIPPING | HIGH DEFINITION MODE |
| NORMAL STRIPPING | HFR MODE |
| OTHER SCENES | (NORMAL MODE) |

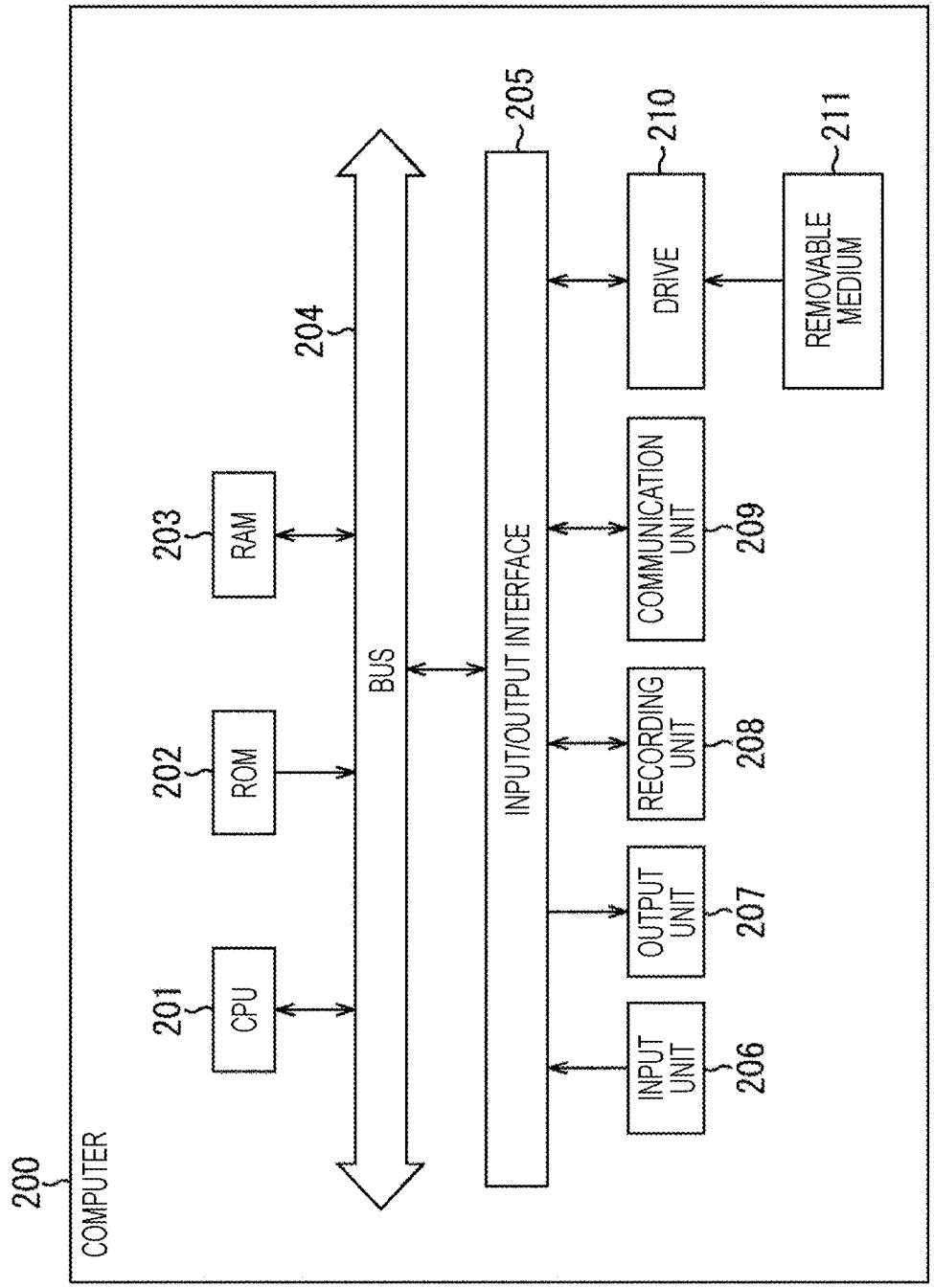

INFORMATION PROCESSING APPARATUS, INFORMATION PROCESSING METHOD, AND ENDOSCOPE SYSTEM FOR PROCESSING IMAGES BASED ON SURGICAL SCENES

CROSS-REFERENCE TO RELATED APPLICATIONS

The present application is a continuation of U.S. application Ser. No. 15/761,438, filed Mar. 20, 2018, which is based on PCT filing PCT/JP2016/080496, filed Oct. 14, 2016, which claims priority to JP 2015-213767, filed Oct. 30, 2015, the entire contents of each are incorporated herein by reference.

TECHNICAL FIELD

The present technology relates to an information processing apparatus, an information processing method, and an endoscope system, and more particularly relates to an information processing apparatus, an information processing method, and an endoscope system capable of providing optimal video images to an operator in accordance with surgical scenes.

BACKGROUND ART

As a technique for obtaining a high definition image, a technique referred to as pixel shift processing is known (for example, refer to Patent Documents 1 and 2).

CITATION LIST

Patent Document

Patent Document 1: Japanese Patent Application Laid-Open No. 2010-268244
Patent Document 2: Japanese Patent Application Laid-Open No. 2011-95073

SUMMARY OF THE INVENTION

Problems to be Solved by the Invention

In a case where an imaging system capable of performing pixel shift processing is used as an endoscopic imaging system in an endoscopic surgery system that supports an operator or the like who performs a surgery using an endoscope, there are cases where providing high definition video images is not appropriate depending on surgical scenes, and this produces a demand for a technique capable of providing optimal video images to the operator in accordance with surgical scenes.

The present technology has been made in view of this situation and is intended to be able to provide an optimal video image to an operator in accordance with surgical scenes.

Solutions to Problems

An information processing apparatus according to the present technology includes: a processing mode determination unit that determines, in accordance with surgical scenes, a processing mode for an in-vivo image captured by an imaging apparatus including an imaging element arranged so as to enable pixel shift processing; and a processing unit that processes an image output from the imaging apparatus, in accordance with the processing mode.

An information processing method according to the present technology is an information processing method of an information processing apparatus, the method including steps of: determining, by the information processing apparatus in accordance with surgical scenes, a processing mode for an in-vivo image captured by an imaging apparatus including an imaging element arranged so as to enable pixel shift processing; and processing an image output from the imaging apparatus, by the information processing apparatus in accordance with the processing mode.

An endoscope system according to the present technology is an endoscope system including an endoscope and an information processing apparatus, in which the endoscope includes: an imaging element arranged so as to enable pixel shift processing; and a control unit that controls the imaging element, the information processing apparatus includes: a processing mode determination unit that determines a processing mode for an in-vivo image captured by the endoscope, in accordance with surgical scenes; and a processing unit that processes an image output from the endoscope, in accordance with the processing mode, and the control unit controls the imaging element in accordance with the processing mode.

In the information processing apparatus, the information processing method, and the endoscope system according to the present technology, a processing mode for an in-vivo image captured by an imaging apparatus including an imaging element arranged so as to enable pixel shift processing is determined in accordance with surgical scenes, and an image output from the imaging apparatus is processed in accordance with the processing mode.

Effects of the Invention

According to the present technology, it is possible to provide an optimal video image to an operator in accordance with surgical scenes.

Note that effects described herein are non-restricting. The effects may be any effects described in the present disclosure.

BRIEF DESCRIPTION OF DRAWINGS

FIG. 4 is a diagram illustrating an exemplary correspondence table in a case where a single-chip sensor is applied.

FIG. 6 is a diagram illustrating an exemplary correspondence table in a case where a three-chip sensor is applied.

FIG. 12 is a diagram illustrating an exemplary configuration of a computer.

MODE FOR CARRYING OUT THE INVENTION

Hereinafter, embodiments of the present technology will be described with reference to the drawings. Note that the description will be given in the following order.

1. System configuration
2. First Embodiment: determination of processing mode using external signal
    (1) Case where single-chip sensor is applied
    (2) Case where three-chip sensor is applied
3. Second embodiment: determination of processing mode by scene recognition
4. Modification
5. Configuration of computer

1. System Configuration (Exemplary Configuration of Endoscopic Surgery System)

Figure 1:
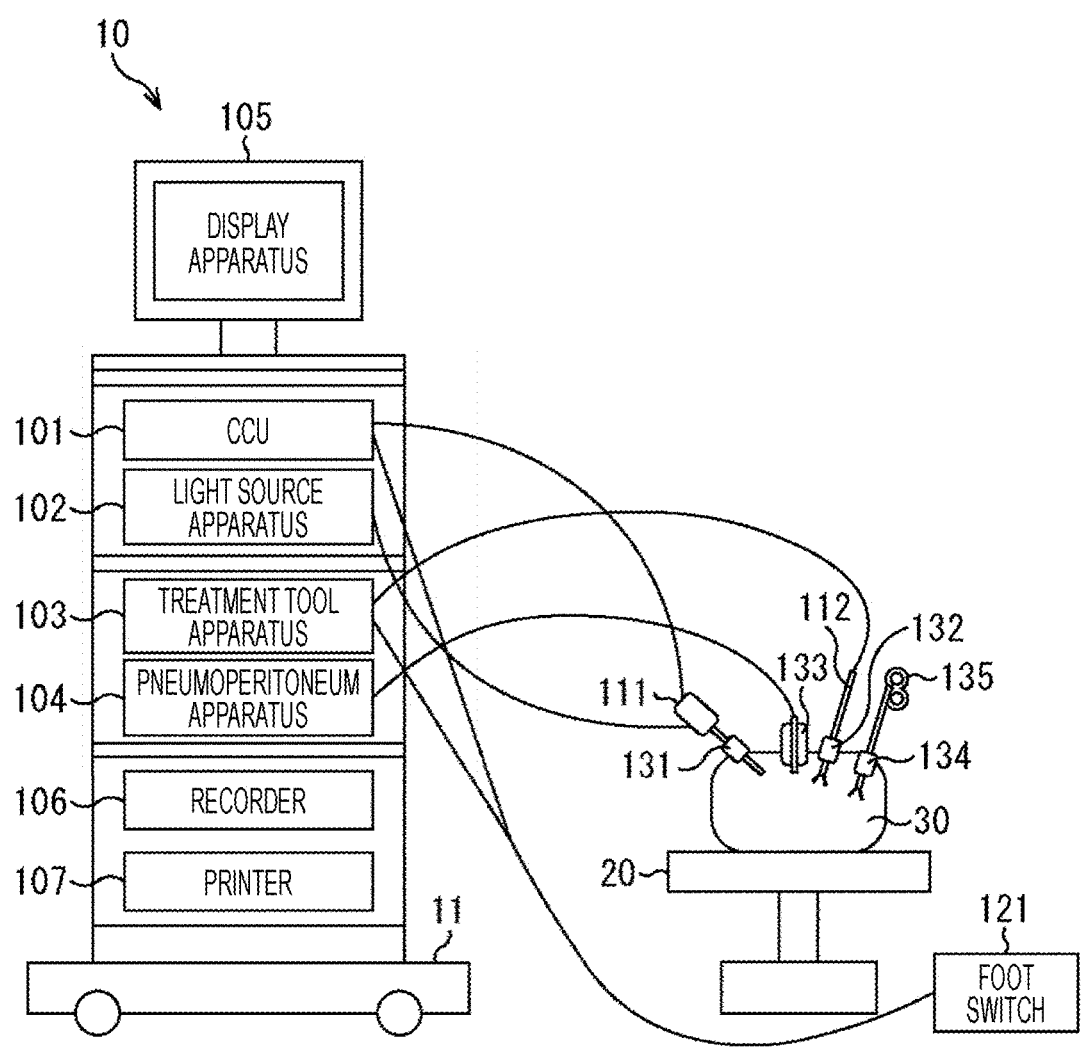
FIG. 1 is a diagram illustrating an embodiment of an endoscopic surgery system according to the present technology.

FIG. 1 is a diagram illustrating an embodiment of an endoscopic surgery system according to the present technology.

An endoscopic surgery system 10 is a system arranged in a surgery room and configured to support an operator performing an endoscopic surgery on an affected site included in an abdomen 30 of a patient lying on a patient bed 20, for example.

In FIG. 1, the endoscopic surgery system 10 includes a camera control unit (CCU) 101, a light source apparatus 102, a treatment tool apparatus 103, a pneumoperitoneum apparatus 104, a display apparatus 105, a recorder 106, and a cart 11 on which a printer 107 is mounted. Moreover, the endoscopic surgery system 10 includes an endoscope (laparoscope) 111, an energy treatment tool 112, and a foot switch 121. Additionally, tools such as trocars 131 to 134 and forceps 135 are used by an operator, or the like, at the time of surgery.

In the endoscopic surgery system 10, the CCU 101 is connected to the endoscope 111 via a camera cable. Note that the CCU 101 may be wirelessly connected to the endoscope 111. The CCU 101 receives an intraoperative image captured by the endoscope 111 and transmitted via the camera cable, and supplies the received image to the display apparatus 105.

The display apparatus 105 includes a stationary 2D display, a head mount display, and the like. The display apparatus 105 displays an intraoperative image, or the like, supplied from the CCU 101. In addition, the CCU 101 supplies the received intraoperative image to the recorder 106 or the printer 107, as necessary.

The light source apparatus 102 is connected to the endoscope 111 via a light guide cable. The light source apparatus 102 switches light of various wavelengths and emits the light to the endoscope 111.

The treatment tool apparatus 103 is a high frequency output device, and is connected to the energy treatment tool 112 and the foot switch 121 via a cable. The treatment tool apparatus 103 outputs a high frequency current to the energy treatment tool 112 in response to an operation signal supplied from the foot switch 121.

The pneumoperitoneum apparatus 104 includes insufflation and suction units and supplies air into the abdomen 30 from a hole of the trocar 133 as an opening tool attached to an abdominal wall of the abdomen 30.

The recorder 106 records an intraoperative image supplied from the CCU 101. The printer 107 prints the intraoperative image supplied from the CCU 101.

The endoscope 111 includes an imaging unit and an optical system such as an illumination lens. The endoscope 111 is inserted into the abdomen 30 as a surgical target from the hole of the trocar 131 attached to the abdominal wall of the abdomen 30. The optical system of the endoscope 111 applies light emitted from the light source apparatus 102 to the inside of the abdomen 30, and the imaging unit captures an image inside the abdomen 30 as an intraoperative image.

The endoscope 111 supplies the intraoperative image to the CCU 101 via the camera cable. This procedure displays the intraoperative image captured by the endoscope 111 on the display apparatus 105, so as to enable the operator to perform treatment such as resection of an affected site inside the abdomen 30 using the energy treatment tool 112 while viewing the image inside the abdomen 30 in real time.

The energy treatment tool 112 includes an electric scalpel and the like. The energy treatment tool 112 is inserted into the abdomen 30 from the hole of the trocar 132 attached to the abdominal wall of the abdomen 30. The energy treatment tool 112 modifies or cuts the inside of the abdomen 30 using electrical heat.

The forceps 135 are inserted into the abdomen 30 from the hole of the trocar 134 attached to the abdominal wall of the abdomen 30. The forceps 135 grip the inside of the abdomen 30. The endoscope 111, the energy treatment tool 112, and the forceps 135 are gripped by an operator, an assistant, a scope specialist, a robot, or the like.

The foot switch 121 receives operation by a foot of an operator, an assistant, or the like. The foot switch 121 supplies an operation signal indicating the received operation to the CCU 101 and the treatment tool apparatus 103. That is, the foot switch 121 controls the CCU 101, the treatment tool apparatus 103, or the like, triggered by the operation by the foot of the operator, the assistant, or the like.

The configuration of the endoscopic surgery system 10 is as described above. By using the endoscopic surgery system 10, the operator can excise the affected site in the abdomen 30 without performing abdominal surgery of cutting and opening the abdominal wall.

Hereinafter, a detailed configuration of the endoscopic surgery system 10 in FIG. 1 will be described focusing on a configuration of the CCU 101 and the endoscope 111. Moreover, processing in the CCU 101 and the endoscope 111 is performed following a processing mode determined in accordance with surgical scenes, and the processing mode is determined either in accordance with an external signal or in accordance with scene recognition. Accordingly, in the following description, determination of the processing mode using an external signal will be first described as a first embodiment, and thereafter, determination of the processing mode by scene recognition will be described as a second embodiment.

2. First Embodiment: Determination of Processing Mode Using External Signal (Exemplary Configuration of CCU and Endoscope)

Figure 2:
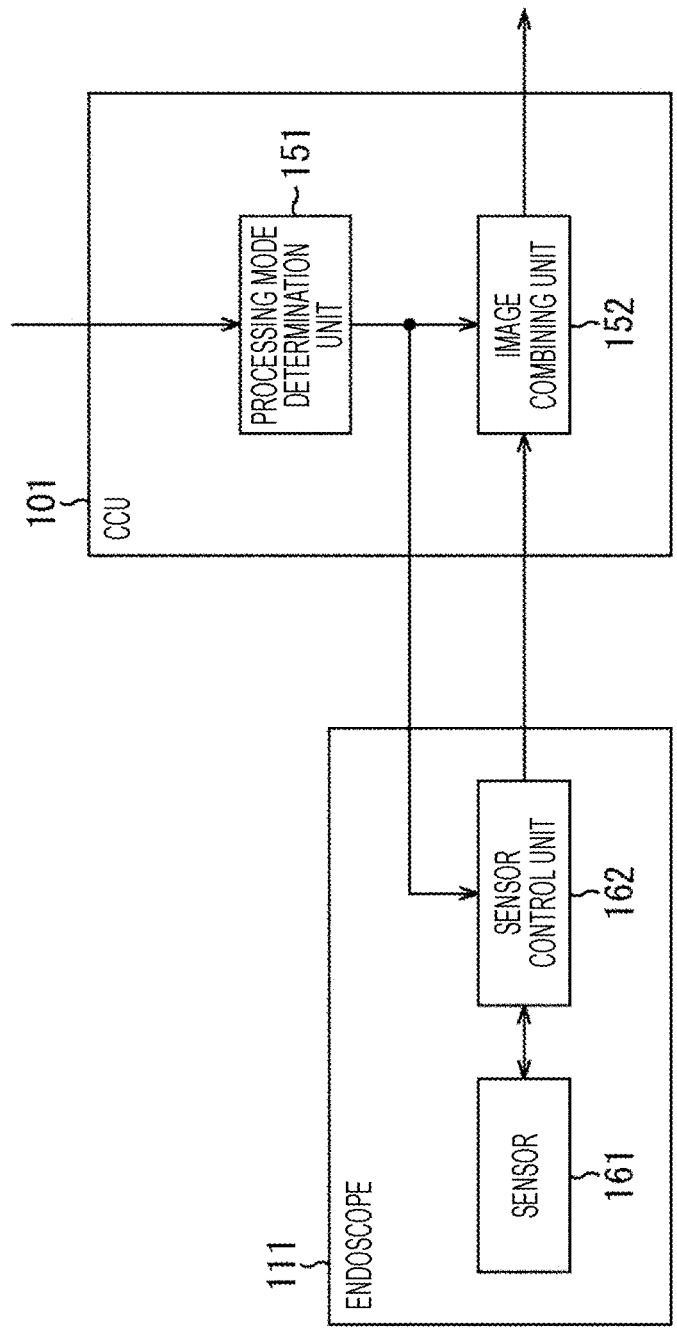
FIG. 2 is a diagram illustrating a detailed exemplary configuration of a CCU and an endoscope according to a first embodiment.

FIG. 2 is a diagram illustrating a detailed exemplary configuration of the CCU 101 and the endoscope 111 according to the first embodiment.

The CCU 101 includes a processing mode determination unit 151 and an image combining unit 152. Moreover, the endoscope 111 includes a sensor 161 and a sensor control unit 162.

The processing mode determination unit 151 determines a processing mode corresponding to the surgical scene in accordance with an external signal input from the outside of the CCU 101. The processing mode determination unit 151 supplies the determined processing mode to the image combining unit 152 and to the sensor control unit 162 of the endoscope 111.

Note that the external signal includes an operation signal corresponding to processing mode switching operation performed by an operator or an assistant, for example. For example, in a case where operation on an input unit (user interface: UI) is received from the operator, the assistant, or the like, the operation signal is to be input to the processing mode determination unit 151 as an external signal.

Moreover, the external signal includes a light source switching signal supplied from the light source apparatus 102 (FIG. 1). For example, in a case where the light source is switched in accordance with observation such as narrow-band imaging (NBI), fluorescence observation in response to operation by the operator, or the like, a switching signal is to be input as an external signal to the processing mode determination unit 151.

Furthermore, the external signal includes a signal indicating power on-off of the energy treatment tool 112 such as an electric scalpel connected to the treatment tool apparatus 103 (FIG. 1) via a cable. For example, in a case where power of the energy treatment tool 112 such as an electric scalpel is turned on or off, a signal indicating the power on/off is to be input to the processing mode determination unit 151 as an external signal.

Moreover, the processing mode determination unit 151 stores a table (hereinafter referred to as a correspondence table) associating a surgical scene with a processing mode. In a case where an external signal is input from the outside of the CCU 101, the processing mode determination unit 151 determines a processing mode corresponding to a surgical scene specified by the external signal with reference to the correspondence table.

Furthermore, although details will be described below with reference to FIG. 4, FIG. 6 or the like, the correspondence table associates a surgical scene such as narrowband imaging (NBI), fluorescence observation, suturing, and stripping with a processing mode such as a high definition mode and a high frame rate (HFR) mode. As the processing modes, a mode according to processing details of image processing such as the presence or absence of pixel shift processing, a frame rate (unit: frame per second (fps)) of an output image (intraoperative image), resolution of the output image (intraoperative image) is set.

The sensor control unit 162 controls the sensor 161 on the basis of the processing mode supplied from the processing mode determination unit 151. Moreover, the sensor control unit 162 supplies an image signal supplied from the sensor 161 to the image combining unit 152 of the CCU 101 via the camera cable.

Examples of the sensor 161 include a solid-state imaging element (imaging element) such as a complementary metal oxide semiconductor (CMOS) image sensor and a charge coupled device (CCD) image sensor.

The sensor 161 includes, for example, an image array unit including a plurality of two-dimensionally arranged pixels having photoelectric conversion elements (photodiodes) that receives incident light from a lens, a peripheral circuit unit that performs pixel drive, analog/digital (A/D) conversion, and the like. The sensor 161 uses photoelectric conversion elements to photoelectrically convert light that has passed through the lens and focused on a light receiving surface, applies predetermined signal processing to covert the light into an image signal and supplies the obtained image signal (image signal of in-vivo image) to the sensor control unit 162.

Note that it is possible to use as the imaging system of the endoscope 111, a single-chip sensor 161 (hereinafter also described as a sensor 161-1) or a three-chip sensor 161 (hereinafter also described as a sensor 161-3). The single-chip method is a method using a single sensor (solid-state imaging element) having each of pixels of RGB as the sensor 161-1. In addition, the three-chip method is a method using three sensors (solid-state imaging elements) having pixels each having each of components of RGB, as the sensor 161-3.

Moreover, the imaging system of the endoscope 111 can employ a technique of pixel shift processing. With this pixel shift processing technique, it is possible to obtain a high definition image.

Hereinafter, a method of temporally shifting the single-chip sensor 161-1 (single sensor) in a case where the single-chip sensor 161-1 is applied in the imaging system of the endoscope 111 will be referred to as a single-chip pixel shift method. Moreover, in a case where the three-chip sensor 161-3 is applied in the imaging system of the endoscope 111, a method of generating optical phase shifts by the three-chip sensor 161-3 (three sensors corresponding to the RGB components) and simultaneously imaging each of planes in an RGB phase shifted state using the three-chip sensor 161-3 (three sensors corresponding to the RGB components) will be referred to as a three-chip pixel shift method.

For example, in the case where the single-chip sensor 161-1 is applied in the imaging system of the endoscope 111, the sensor control unit 162 controls the single-chip pixel shift in the single-chip sensor 161-1 in accordance with the processing mode supplied from the processing mode determination unit 151. Herein, in the case of performing single-chip pixel shift in accordance with the processing mode, the sensor control unit 162 controls the driving unit such as a piezoelectric driving apparatus to move the single-chip sensor 161-1 in units of pixels.

Moreover, for example, in the case of using the three-chip sensor 161-3 in the imaging system of the endoscope 111, the sensor control unit 162 performs shutter control or the like of the endoscope 111 in accordance with the processing mode.

An image signal is supplied from the sensor control unit 162 of the endoscope 111 to the image combining unit 152 via the camera cable. On the basis of the processing mode supplied from the processing mode determination unit 151, the image combining unit 152 performs predetermined image processing on the image signal from the sensor control unit 162, and outputs the processed signal as an output image (intraoperative image).

For example, in the case where the single-chip sensor 161-1 is applied in the imaging system of the endoscope 111, the image combining unit 152 performs predetermined image processing corresponding to the processing mode, such as processing of adding an image signal output from the single-chip sensor 161-1 (single sensor). Moreover, for example, in a case where the three-chip sensor 161-3 is applied in the imaging system of the endoscope 111, the image combining unit 152 performs predetermined image processing corresponding to the processing mode, such as processing of combining an image signal output from the three-chip sensor 161-3 (three sensors corresponding to RGB components).

In the endoscopic surgery system 10 (FIG. 1), the CCU 101 and the endoscope 111 are configured as described above. Next, the imaging system of the endoscope 111 in a case where the single-chip sensor 161-1 is applied and in a case where the three-chip sensor 161-3 is applied will be sequentially described in this order.

(1) Case where Single-Chip Sensor is Applied (Outline of Single-Chip Pixel Shift Method)

Figure 3:
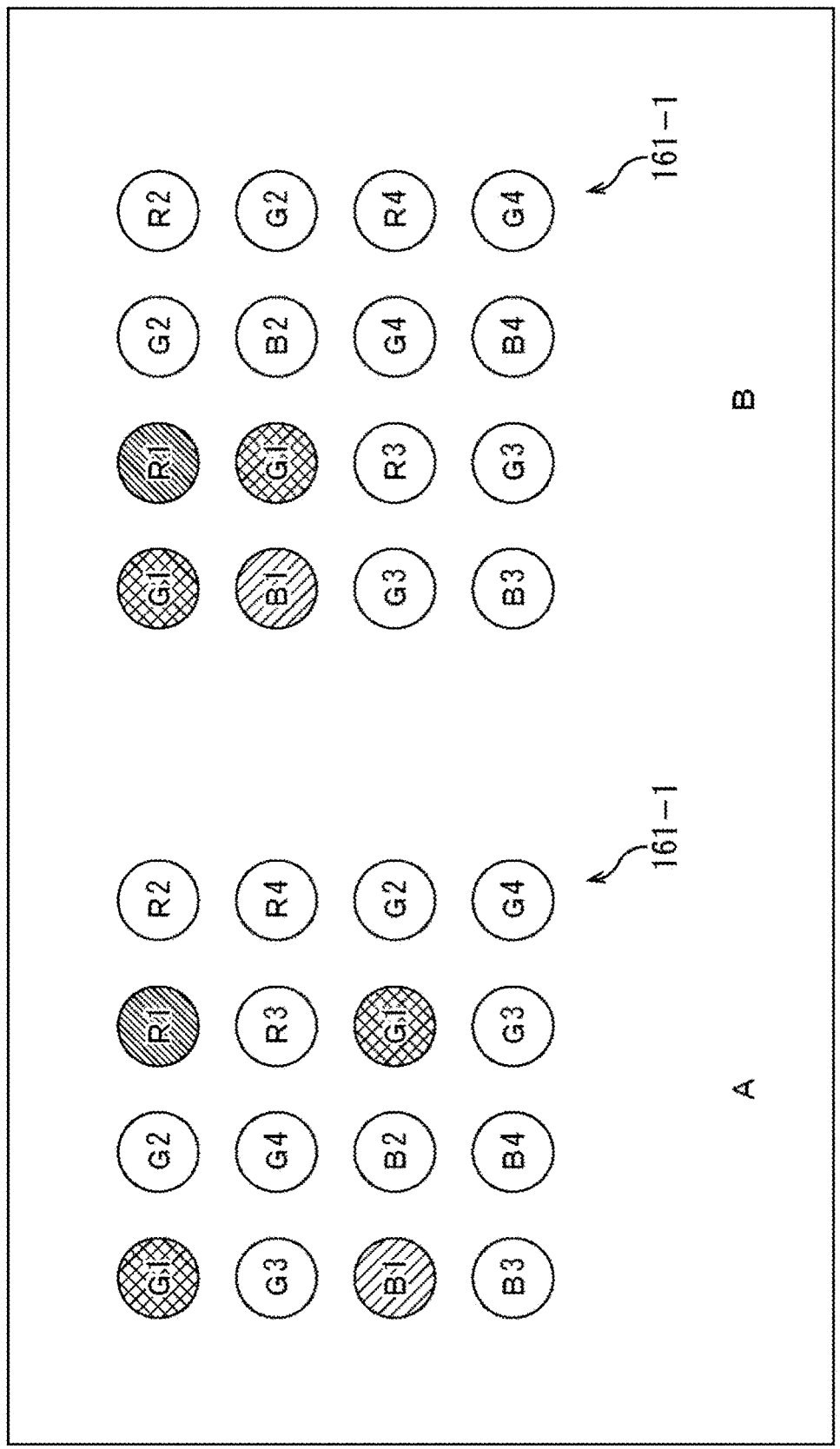
FIG. 3 is a view illustrating an outline of a single-chip pixel shift method.

FIG. 3 is a diagram illustrating an outline of a single-chip pixel shift method.

FIG. 3 illustrates two examples of a single-plate pixel shift method of temporally shifting a single solid-state imaging element in A of FIG. 3 and B of FIG. 3.

Herein, 4×4 pixels are illustrated as representative examples, among a plurality of pixels two-dimensionally arranged on the light receiving surface of the single-chip sensor 161-1 (solid-state imaging element).

Moreover, an R pixel capable of obtaining a red (R) image signal is described as "R". Similarly, a G pixel capable of obtaining a green (G) image signal is described as "G", while a B pixel capable of obtaining a blue (B) image signal is described as "B".

(A) Single-Chip Pixel Shift Method A

In A of FIG. 3, the numerals 1 to 4 described in individual pixels represent the number of times of imaging. For example, image signals corresponding to four pixels with patterns in odd rows and odd columns, that is, pixel G1, pixel R1, pixel B1, and pixel G1, are to be obtained by first imaging. Note that by focusing on these four pixels, a Bayer pattern is generated in which the pixels G1 are arranged in a checkerboard pattern, with the pixels R1 and the pixels B1 alternately arranged in a row in the remaining portion.

After the first imaging, the single-chip sensor 161-1 is moved by one pixel in the right direction (row direction) in the figure, whereby image signals corresponding to four pixels in the odd rows and the even columns arranged in the Bayer pattern, that is, pixel G2, pixel R2, pixel B2, and pixel G2, are obtained by second imaging.

Moreover, after the second imaging, the single-chip sensor 161-1 is moved by one pixel in the left diagonal downward direction in the figure, whereby image signals corresponding to four pixels in the even rows and the odd columns arranged in the Bayer pattern, that is, pixel G3, pixel R3, pixel B3, and pixel G3, are obtained by third imaging.

Subsequently, after the third imaging, the single-chip sensor 161-1 is moved by one pixel in the right direction (row direction) in the figure, whereby image signals corresponding to four pixels in the even rows and the even columns arranged in the Bayer pattern, that is, pixels G4, pixel R4, pixel B4, and pixel G4, are obtained by fourth imaging.

In this manner, by shifting the single-chip sensor 161-1 (solid-state imaging element) in units of pixels to repeat four shots of imaging in total at each of the positions in the single-chip pixel shift method A illustrated in A of FIG. 3, image signals corresponding to four shots of imaging can be obtained from each of the pixels, making it possible to obtain quadrupled output image resolution.

(B) Single-Chip Pixel Shift Method B

In B of FIG. 3, similarly to A of FIG. 3, the numerals 1 to 4 described in individual pixels represent the number of times of imaging. For example, image signals corresponding to four pixels in an upper left corner arranged in the Bayer pattern, that is, pixel G1, pixel R1, pixel B1, and pixel G1 are to be obtained by first imaging.

After the first imaging, the single-chip sensor 161-1 is moved by two pixels in the upper right direction (row direction) in the figure, whereby image signals corresponding to four pixels in an upper right corner arranged in the Bayer pattern, that is, pixel G2, pixel R2, pixel B2, and pixel G2, are obtained by second imaging.

Moreover, after the second imaging, the single-chip sensor 161-1 is moved by two pixels in the left diagonal downward direction in the figure, whereby image signals corresponding to four pixels in the lower left corner arranged in the Bayer pattern, that is, pixels G3, pixel R3, pixel B3, and pixel G3, are obtained by third imaging.

Subsequently, after the third imaging, the single-chip sensor 161-1 is moved by two pixels in the right direction (row direction) in the figure, whereby image signals corresponding to four pixels in the lower right corner arranged in the Bayer pattern, that is, pixel G4, pixel R4, pixel B4, and pixel G4, are obtained by fourth imaging.

In this manner, in the single-chip pixel shift method B illustrated in B of FIG. 3, by shifting the single-chip sensor 161-1 (solid-state imaging element) in units of pixels to repeat four shots of imaging in total at each of the positions, image signals corresponding to four shots of imaging can be obtained from each of the pixels, making it possible to obtain quadrupled output image resolution.

Note that the single-chip pixel shift method A in A of FIG. 3 and the single-chip pixel shift method B in B of FIG. 3 are exemplary single-chip pixel shift methods of the single-chip sensor 161-1, and it is allowable to employ other method to perform single-chip pixel shift of the single-chip sensor 161-1.

(Correspondence Table of Single-Chip Sensor)

FIG. 4 is a diagram illustrating an exemplary correspondence table in a case where the single-chip sensor 161-1 is applied in the imaging system of the endoscope 111.

The correspondence table in FIG. 4 is a table associating surgical scenes and processing modes in a case where the single-chip sensor 161-1 is applied. Note that there are four types of processing modes in a case where the single-chip sensor 161-1 is applied, that is, a normal mode, a high definition mode, a high frame rate (HFR) mode, and a noise reduction (NR) mode. Note that the single-chip pixel shift illustrated in FIG. 3 is performed in the high definition mode among these processing modes.

The normal mode is a mode in which single-chip pixel shift is not performed and an image (image data) captured at 60 fps is output at 60 fps. For example, in A of FIG. 3 (or B of FIG. 3), imaging is performed selectively at each of the pixel positions at which the numeral 1 is described, that is, at pixel G1, pixel R1, pixel B1, and pixel G1, and an output image obtained from image signals output from these pixels is output at 60 fps.

The high definition mode is a mode in which single-pixel shift is performed and a high definition image (image data) with quadrupled resolution is output at 60 fps. For example, in A in FIG. 3 (or B in FIG. 3), the single-chip sensor 161-1 is shifted in units of pixels in 1/60 seconds at the position of pixel in which 1 to 4 numerals are described, and four shots of imaging in total is repeated at each of the positions. With this imaging, a high definition image having quadrupled resolution compared with the normal mode or the like is generated and output at 60 fps as an output image. That is, this high definition mode is applied to perform the single-chip pixel shift illustrated in FIG. 3 to output an output image with higher resolution compared with other modes.

Furthermore, the high definition images obtained in the high definition mode include not merely high definition (HD) video images, but also, for example, ultra high definition (UHD) video images having 4K resolution (for example 3840 in width×2160 in height) and 8K resolution (for example 7680 in width×4320 in height).

The HFR mode is a mode in which single-chip pixel shift is not performed and the image (image data) is obtained by four shots of imaging during 1/60 second and then output at 240 fps. For example, in A of FIG. 3 (or B of FIG. 3), four shots of imaging are performed selectively at each of the pixel positions at which the numeral 1 is described, that is, at pixel G1, pixel R1, pixel B1, and pixel G1 during 1/60 second, and an output image obtained from the image signal output from these pixels is output at 240 fps. That is, in this HFR mode, the output image can be output at a higher frame rate than in other modes.

The NR mode is a mode in which single-chip pixel shift is not performed and the four images (image data) are obtained by four shots of imaging during 1/60 second, added and then output at 60 fps. For example, in A of FIG. 3 (or B of FIG. 3), four shots of imaging are performed selectively at each of the pixel positions at which the numeral 1 is described, that is, at pixel G1, pixel R1, pixel B1, and pixel G1 during 1/60 second, and the output image obtained by adding the image signals output from these pixels is output at 60 fps. That is, in this NR mode, the output image with less noise compared with other modes can be output.

In the correspondence table of FIG. 4, each of surgical scenes is associated with each of these processing modes. That is, each of the scenes of the narrowband imaging (NBI) and fluorescence observation is associated with the processing mode of either the high definition mode or the NR mode. In addition, the suturing scene is associated with the processing mode of the high definition mode.

The scope movement scene is associated with the processing mode of the HFR mode. Moreover, the careful stripping scene is associated with the processing mode of the high definition mode, while the normal stripping scene is associated with the processing mode of the HFR mode.

Note that the normal mode is associated with scenes other than the above-described surgical scenes, that is, scenes other than narrowband imaging, fluorescence observation, suturing, scope movement, careful stripping, and normal stripping scenes.

In this manner, in the correspondence table of FIG. 4, the high definition mode and the NR mode are applied to provide high definition images and images with less noise for the scenes where the scope movement is relatively small and the operator wishes to watch in more detail, such as narrowband imaging (NBI), fluorescence observation, careful stripping, and suturing. Moreover, for example, the narrowband imaging (NBI) performs observation with limited amount of light, that is, in a dark condition, leading to a phenomenon of increasing noise in an output image. In this case, with a setting to select (determine) the NR mode as the processing mode, it is possible to remove the noise included in the output image.

Moreover, in the correspondence table of FIG. 4, for example, the HFR mode is applied to provide an image (high frame rate image) enabling the motion to appear smoother for a scene including a large motion of a scope such as scope movement or for a normal stripping scene. With this mode, for example, fatigue of the operator or assistant can be reduced.

In this manner, it is not always a good choice to display a high definition image (video image) and there is a case where an image (video image) with a higher frame rate or an image (video image) with less noise is more suitable depending on the surgical scene. Therefore, according to the present technology, an appropriate processing mode corresponding to the surgical scene is to be determined by the correspondence table of FIG. 4.

Note that in a case where the single-chip sensor 161-1 is applied, the processing mode determination unit 151 of the CCU 101 stores the correspondence table (FIG. 4) beforehand so as to determine the processing mode corresponding to the surgical scene specified by the external signal.

The correspondence table in a case where the single-chip sensor 161-1 is applied in the imaging system of the endoscope 111 has been described above.

(2) Case where Three-Chip Sensor is Applied (Outline of Three-Chip Pixel Shift Method)

Figure 5:
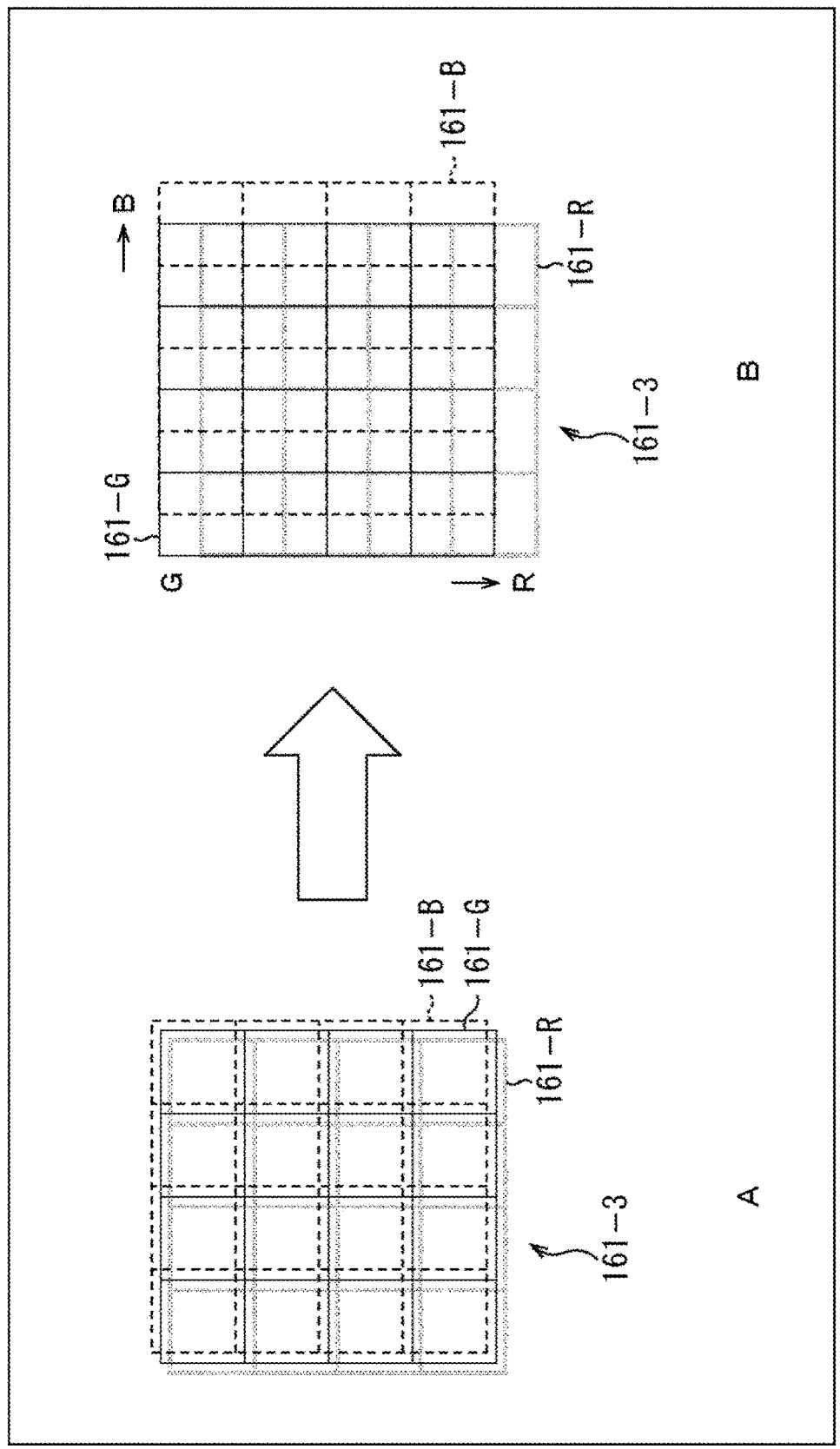
FIG. 5 is a diagram illustrating an outline of a three-chip pixel shift method.

FIG. 5 is a diagram illustrating an outline of the three-chip pixel shift method.

As illustrated in A of FIG. 5, the three-chip sensor 161-3 functions such that light passing through the lens is divided into an R component, a G component, and a B component by a prism, so as to be received by a sensor 161-R, a sensor 161-G, and a sensor 161-B, respectively, corresponding to each of the components, allowing an image signal of each of the components to be output from each of the sensors.

That is, A of FIG. 5 illustrates an exemplary configuration as the three-chip sensor 161-3 including the sensor 161-R for receiving R component light, the sensor 161-G for receiving G component light, and the sensor 161-B for receiving the B component light. In this manner, the three-chip sensor 161 includes dedicated sensors (sensor 161-R, sensor 161-G, and sensor 161-B) applicable for each of the three primary colors of RGB, leading to an advantage of achieving excellent color reproducibility and resolution.

In addition, as illustrated in B of FIG. 5, in the case of implementing the three-chip pixel shift method by the three-chip sensor 161-3, for example, the sensor 161-R is shifted by ½ pixel downward (in column direction) in the drawing and the sensor 161-B is shifted by ½ pixel rightward (in row direction) in the drawing with respect to the sensor 161-G as a reference.

That is, as illustrated in B of FIG. 5, the sensor 161-R and the sensor 161-B are shifted with respect to the sensor 161-G to generate an optical phase shift, and individual planes are simultaneously imaged by the sensor 161-R, the sensor 161-G, and the sensor 161-B in a state where the phases of RGB are shifted, whereby a high definition image can be obtained. Note that in the following description, it is assumed that three-chip pixel shift is performed in the three-chip sensor 161-3 as illustrated in B of FIG. 5. In addition, while the three-chip sensor 161-3 will be described as an example in the following, it is also allowable to use, for example, three or more sensors (solid-state imaging elements) in the case of using an infrared (IR) component in addition to the RGB components.

(Correspondence Table of Three-Chip Sensor)

FIG. 6 is a diagram illustrating an exemplary correspondence table in a case where the three-chip sensor 161-3 is applied in the imaging system of the endoscope 111.

The correspondence table in FIG. 6 is a table associating surgical scenes and processing modes in a case where the three-chip sensor 161-3 is applied. Note that the processing mode in a case where the three-chip sensor 161-3 is applied includes two types of modes, namely, the high definition mode and the HFR mode.

The high definition mode is a mode of imaging each of RGB planes at a same timing, generating a high definition image from the RGB plane images, and outputting the image as an output image at 60 fps.

Note that the method for generating a high definition image from each of RGB planes with shifted phases, for example, include a method of generating a pixel at a position where no pixel is present using interpolation for each of the plane by a linear filter (Linear Filter) or a general bicubic filter (Bi-Cubic Filter). Note that the technique for generating the high definition image exemplified here is illustrative, and other known methods can be used. For example, Japanese Patent Laid-Open No. 2000-13670 discloses a technique using a linear filter.

Note that the high definition image obtained in this high definition mode includes, for example, UHD video images achieving 4K resolution and 8K resolution as well as HD video images. That is, with the high definition mode, it is possible to output an output image with higher resolution than in the HFR mode. Furthermore, details of the high definition mode will be described below with reference to FIG. 7.

The HFR mode is a mode of combining images of RBG planes having close imaging time among the RBG plane images captured with shifted imaging timings as a result of imaging of RGB planes with different timings and outputting the combined image as an output image at 120 fps. That is, in this HFR mode, it is possible to output an output image at a higher frame rate than in the high definition mode. Furthermore, details of the HFR mode will be described below with reference to FIGS. 7 and 8.

In the correspondence table of FIG. 6, individual surgical scenes are associated with these processing modes. That is, the narrowband imaging (NBI) and fluorescence observation scenes are associated with the processing mode of the high definition mode. In addition, the suturing scene is associated with the processing mode of the high definition mode.

The scope movement scene is associated with the processing mode of the HFR mode. Moreover, the careful stripping scene is associated with the processing mode of the high definition mode, while the normal stripping scene is associated with the processing mode of the HFR mode.

Note that the surgical scenes other than the above, that is, the surgical scenes not associated with the high definition mode or the HFR mode can be associated with the processing mode of the normal mode. In the normal mode, an output image is output without undergoing any special processing.

In this manner, in the correspondence table of FIG. 6, high definition mode is applied to provide high definition images for the scenes where the scope movement is relatively small and the operator wishes to watch in more detail, such as narrowband imaging (NBI), fluorescence observation, careful stripping, and suturing.

Moreover, in the correspondence table of FIG. 6, for example, the HFR mode is applied to provide an image (high frame rate image) enabling the motion to appear smoother for a scene including a large motion of a scope such as scope movement or for a normal stripping scene.

Furthermore, in comparison between the correspondence table (FIG. 4) for application of the single-chip sensor 161-1 and the correspondence table (FIG. 6) for application of the three-chip sensor 161-3, there is a difference in the correspondence table (FIG. 6) for application of the three-chip sensor 161-3 that the NR mode is not included in the processing mode. This is because it is difficult to obtain a plurality of images without shifting pixels due to the structure of the three-chip sensor 161-3.

In this manner, it is not always a good choice to display a high definition image (video image) and there is a case where an image (video image) with a higher frame rate is more suitable depending on the surgical scene. Therefore, according to the present technology, an appropriate processing mode corresponding to the surgical scene is to be determined by the correspondence table of FIG. 6.

Note that in a case where the three-chip sensor 161-3 is applied, the processing mode determination unit 151 of the CCU 101 stores the correspondence table (FIG. 6) beforehand so as to determine a processing mode corresponding to the surgical scene specified by the external signal.

The correspondence table used in a case where the three-chip sensor 161-3 is applied in the imaging system of the endoscope 111 has been described above.

(RGB Signal Output Timing for Each of Processing Modes)

Figure 7:
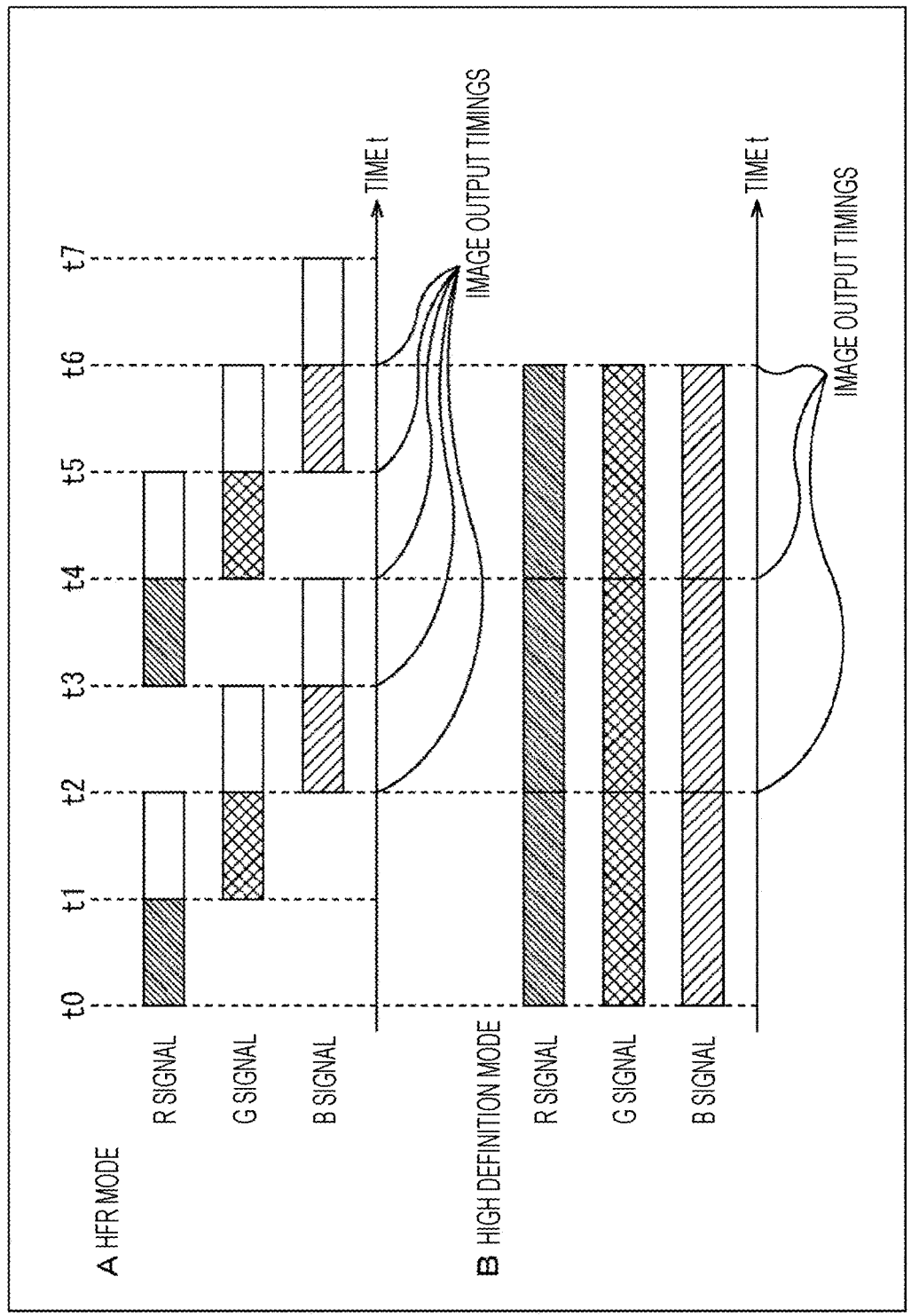
FIG. 7 is a timing chart illustrating RGB signal output timings for each of processing modes.

FIG. 7 is a timing chart illustrating RGB signal output timings for each of the processing modes. In FIG. 7, the time direction is a direction from the left side to the right side in the figure.

A of FIG. 7 is a timing chart illustrating RGB signal output timings for the HFR mode. Moreover, B of FIG. 7 is a timing chart illustrating RGB signal output timings for the high definition mode.

Moreover, in the timing chart of A of FIG. 7 and B of FIG. 7, an image signal corresponding to the R component output from the sensor 161-R is described as an "R signal". Similarly, an image signal corresponding to the G component output from the sensor 161-G is described as a "G signal", while an image signal corresponding to the B component output from the sensor 161-B is described as a "B signal".

That is, in the high definition mode timing chart in B of FIG. 7 illustrating the outputs of the R signal, the G signal, and the B signal in chronological order, the sensor 161-R, the sensor 161-G, and the sensor 161-B are capable of outputting the R signal, the G signal, and the B signal, respectively, at a same timing because the shutter is in a released state in the three-chip sensor 161-3 in the endoscope 111.

With this configuration, the high definition mode enables imaging of each of the RGB planes at a same timing, generating a high definition image from the obtained RGB plane images, and outputting the image at 60 fps as an output image. For example, focusing on the period from time t2 to time t6 in the timing chart of B of FIG. 7, a high definition image (output image) is to be output at the timing of each of time t2, time t4, and time t6.

In contrast, in the timing chart of the HFR mode in A of FIG. 7 illustrating the outputs of the R signal, the G signal, and the B signal in chronological order, a shutter of the endoscope 111 (three-chip sensor 161-3) is controlled to perform imaging with halved exposure time as compared with the case of the high definition mode, and in addition, at shifted timing for each of the RGB planes.

Furthermore, the RGB plane images captured at close imaging times are to be combined with each other among the RGB plane images captured with shifted imaging timings. Specifically, for example, focusing on the period from time t2 to time t6 in the timing chart of A in FIG. 7, for example, the G signal obtained in the period from time t1 to time t2 is used, at time t2, so as to combine the R signal and the B signal temporally close to the G signal.

Similarly, at time t3, for example, the B signal obtained in the period from time t2 to time t3 is used to combine the R signal and the G signal temporally close to the B signal. Moreover, at time t4, for example, the R signal obtained in the period from time t3 to time t4 is used to combine the G signal and the B signal temporally close to the R signal.

Furthermore, at time t5, for example, the G signal obtained in the period from time t4 to time t5 is used to combine the R signal and the B signal temporally close to the G signal. Moreover, at time t6, for example, the B signal obtained in the period from time t5 to time t6 is used to combine the R signal and the G signal temporally close to the B signal.

In this manner, the HFR mode is capable of imaging with the halved exposure time compared with the high definition mode to capture each of the RGB planes at different timings, combining RGB plane images having close imaging times among the RGB plane images captured with the shifted imaging timings, and outputting the image at 120 fps. For example, focusing on the period from time t2 to time t6 in the timing chart in A of FIG. 7, a high frame rate image (output image) is output at a timing of each of the time from time t2 to time t6.

Note that, comparing the timing chart of the HFR mode in A of FIG. 7 with the timing chart of the high definition mode in B of FIG. 7, the output image is output at the time of time t2, time t4, and time t6 among the period from time t2 to time t6 in the high definition mode, while the output image is output at the timing of each of the time points from time t2 to time t6 in the HFR mode. That is, the frame rate (for example, 120 fps) of the output image in the HFR mode is twice the frame rate (for example, 60 fps) of the output image in the high definition mode.

Note that while the exemplary timing chart in FIG. 7 uses the exposure time in the HFR mode being halved compared with the case in the high definition mode, the exposure time can be further reduced to ⅓, ¼, or the like, to further increase the frame rate of the output image in the HFR mode.

Meanwhile, since images to be combined (R signal, G signal, and B signal) are not images captured at the same timing at the time of combining the RGB plane images having closer imaging times (temporally shifted captured images), there is a case where a subject included in the image moves. Herein, in order to cope with such a case, the image combining unit 152 (FIG. 2) of the CCU 101 has a configuration as illustrated in FIG. 8.

Figure 8:
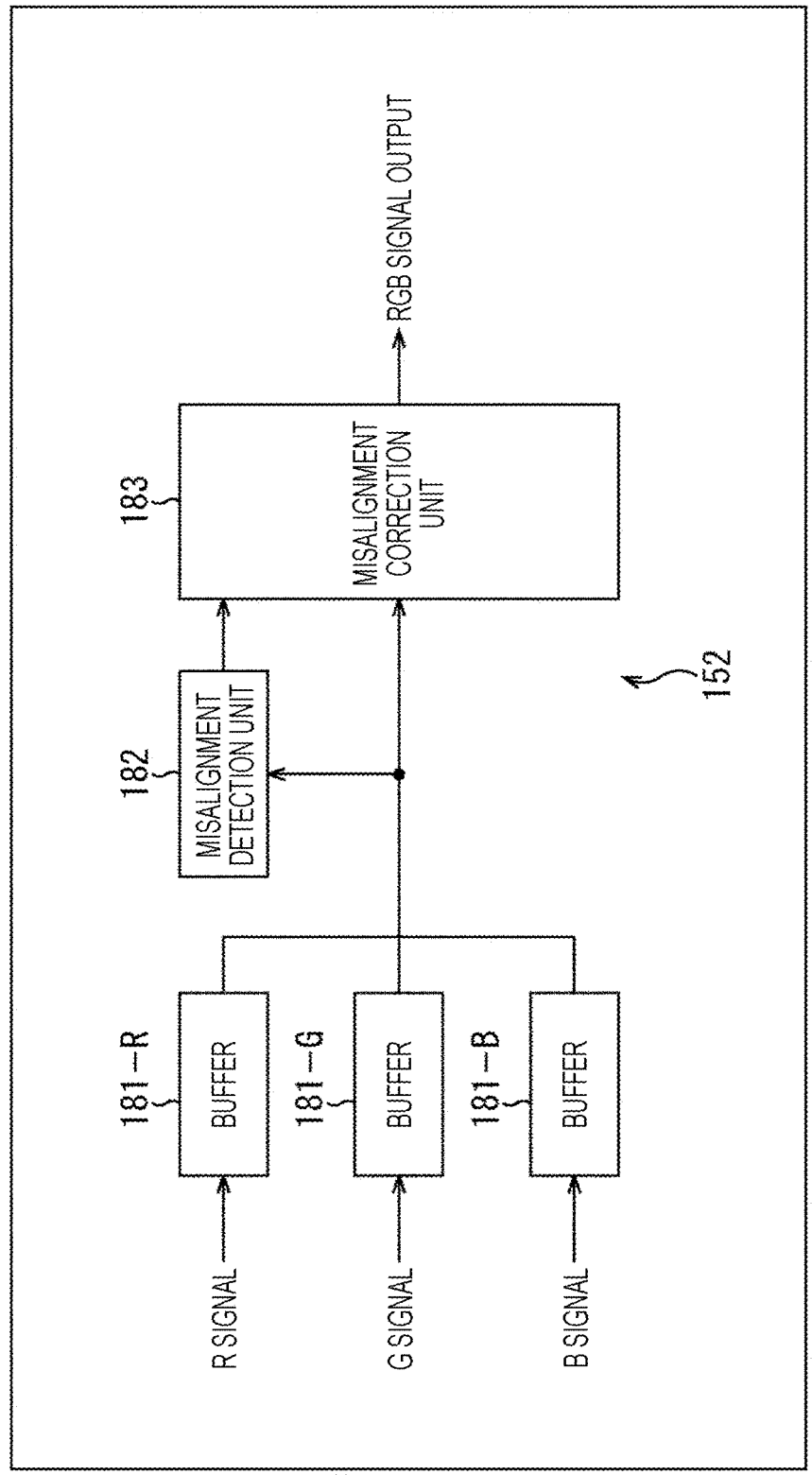
FIG. 8 is a diagram illustrating an exemplary configuration of an image combining unit corresponding to an HFR mode.

In FIG. 8, the image combining unit 152 corresponding to the HFR mode includes a buffer 181-R, a buffer 181-G, a buffer 181-B, a misalignment detection unit 182, and a misalignment correction unit 183.

The buffer 181-R is a buffer to hold the R signal output from the sensor 161-R of the endoscope 111. The buffer 181-G is a buffer to hold the G signal output from the sensor 161-G of the endoscope 111. The buffer 181-B is a buffer to hold the B signal output from the sensor 161-B of the endoscope 111.

For example, in a case where the G signal obtained in the period from time t1 to time t2 is used at time t2 in the timing chart of the HFR mode in A of FIG. 7 described above, the G signal is held in the buffer 181-G, and the R signal and the B signal temporally close to the G signal are held in the buffer 181-R and the buffer 181-B, respectively.

The R signal, the G signal, and the B signal respectively held in the buffer 181-R, the buffer 181-G, and the buffer 181-B are read by the misalignment detection unit 182 and the misalignment correction unit 183.

The misalignment detection unit 182 applies block matching, mutual correlation, or the like, to the R signal, the G signal, and the B signal respectively read from the buffer 181-R, the buffer 181-G, and the buffer 181-B, thereby detecting the misalignment amount of each of the signals for each of the pixels. The misalignment detection unit 182 supplies the misalignment amount of each of the detected signals to the misalignment correction unit 183.

The misalignment correction unit 183 receives inputs of the R signal, the G signal, and the B signal respectively read from the buffer 181-R, the buffer 181-G, and the buffer 181-B, as well as inputs of the misalignment amounts of the individual signals synchronized with these signals, from the misalignment detection unit 182.

On the basis of the misalignment amount of each of the signals from the misalignment detection unit 182, the misalignment correction unit 183 performs misalignment correction for each of the pixels of the R signal, the G signal, and the B signal respectively read from the buffer 181-R, the buffer 181-G, and the buffer 181-B. The misalignment correction unit 183 collectively outputs the R signal, G signal, and B signal aligned with each other by misalignment correction, as an RGB signal (output image).

In this manner, since the images to be combined (R signal, G signal, and B signal) are not images captured at the same timing at the time of combining the RGB plane images with close imaging times, there is a possibility that the subject included in the image moves. Therefore, the image combining unit 152 (FIG. 8) of the CCU 101 processes the R signal, the G signal, and B signal, buffered in each of the buffers 181, using the misalignment detection unit 182 and the misalignment correction unit 183 so as to perform correction to achieve alignment of the position of the subject that has moved. With this configuration, it is possible to output, in the HFR mode, an output image at a timing of 120 fps which is twice the high definition mode, for example.

(Image Combining Processing Flow)

Next, an image combining processing flow according to the first embodiment will be described with reference to the flowchart in FIG. 9.

In step S101, the processing mode determination unit 151 receives an external signal input from the outside of the CCU 101.

Note that the external signal to be provided includes, for example, an operation signal corresponding to processing mode switching operation by an operator or the like, a light source switching signal supplied from the light source apparatus 102 (FIG. 1), or a signal indicating power on-off of the energy treatment tool 112.

In step S102, the processing mode determination unit 151 determines a processing mode corresponding to the surgical scene specified by the external signal received in the processing of step S101 with reference to the correspondence table stored beforehand.

For example, in a case where the single-chip sensor 161-1 is applied in the imaging system of the endoscope 111, the processing mode determination unit 151 determines the processing mode corresponding to the surgical scene with reference to the correspondence table in FIG. 4. Moreover, in a case where the three-chip sensor 161-3 is applied in the imaging system of the endoscope 111, for example, the processing mode determination unit 151 determines the processing mode corresponding to the surgical scene with reference to the correspondence table in FIG. 6.

In step S103, the sensor control unit 162 controls the sensor 161 on the basis of the processing mode determined by the processing in step S102. The sensor 161 outputs an image signal (image signal of an in-vivo image) under the control of the sensor control unit 162.

For example, in a case where the single-chip sensor 161-1 is applied, the sensor control unit 162 controls the single-chip pixel shift corresponding to the processing mode. More specifically, the sensor control unit 162 turns on the pixel shift processing by the single-chip sensor 161-1 in a case where the processing mode is the high definition mode, while the unit turns off the pixel shift processing by the single-chip sensor 161-1 in a case where the processing mode is set to the mode other than the high definition mode.

Moreover, in a case where the three-chip sensor 161-3 is applied, for example, the sensor control unit 162 performs shutter control of the endoscope 111 in accordance with the processing mode. More specifically, in a case where the processing mode is the HFR mode, the sensor control unit 162 controls to halve the exposure time as compared with the case of the high definition mode and controls an imaging timing shift for each of the RGB planes by shutter speeds so as to implement imaging at shifted timing for each of the RGB planes.

In step S104, the image combining unit 152 obtains an image signal output from the endoscope 111 (the sensor 161 thereof) via a camera cable.

In step S105, the image combining unit 152 combines (processes) the image signal obtained by the processing in step S104 on the basis of the processing mode determined by the processing in step S102. The output image obtained by the processing of step S105 is output at a predetermined frame rate.

For example, in a case where the single-chip sensor 161-1 is applied, the image combining unit 152 performs predetermined image processing corresponding to the processing mode. More specifically, in a case where the processing mode is the NR mode, for example, the image combining unit 152 performs image processing of adding image signals obtained by four shots of imaging.

Moreover, for example, in a case where the three-chip sensor 161-3 is applied, the image combining unit 152 performs predetermined image processing corresponding to the processing mode. More specifically, in a case where the processing mode is the high definition mode, for example, the image combining unit 152 performs image processing of combining the R signal, the G signal, and the B signal. Moreover, as described above, in a case where the processing mode is the HFR mode, the image combining unit 152 uses the configuration illustrated in FIG. 8 to perform the processing described with reference to FIG. 8.

In step S106, it is determined whether to finish the processing. In a case where it is determined in step S106 that the processing is not to be finished, the processing returns to step S101 to repeat subsequent processing. In addition, in a case where it is determined in step S106 that the processing is to be finished, the image combining processing of the first embodiment in FIG. 9 is finished.

The image combining processing flow according to the first embodiment has been described above. In the image combining processing, the processing mode determination unit 151 refers to the correspondence table (for example, the correspondence table in FIG. 4 or FIG. 6) to determine the processing mode corresponding to the surgical scene specified by the external signal, and then, the sensor control unit 162 and the image combining unit 152 perform processing corresponding to the processing mode determined by the processing mode determination unit 151. That is, an appropriate processing mode corresponding to the surgical scene is determined by the correspondence table (for example, the correspondence table in FIG. 4 or FIG. 6) and the processing corresponding to the processing mode is performed, making it possible to provide an optimal video image to the operator in accordance with the surgical scenes.

3. Second Embodiment: Determination of Processing Mode by Scene Recognition

Meanwhile, the first embodiment describes a case where a surgical scene is specified by an external signal input from the outside of the CCU 101 to determine the processing mode corresponding to the surgical scene with reference to the correspondence table (for example, the correspondence table in FIG. 4 or FIG. 6). As a method for specifying the surgical scene, it is allowable to use, for example, a method in which a scene recognition processing is performed on an output image (intraoperative image) to specify the surgical scene in accordance with a scene recognition result, other than the method using the external signal.

Accordingly, a method of specifying a surgical scene by scene recognition processing on an output image (intraoperative image) will be described as a second embodiment.

(Exemplary Configuration of CCU and Endoscope)

Figure 10:
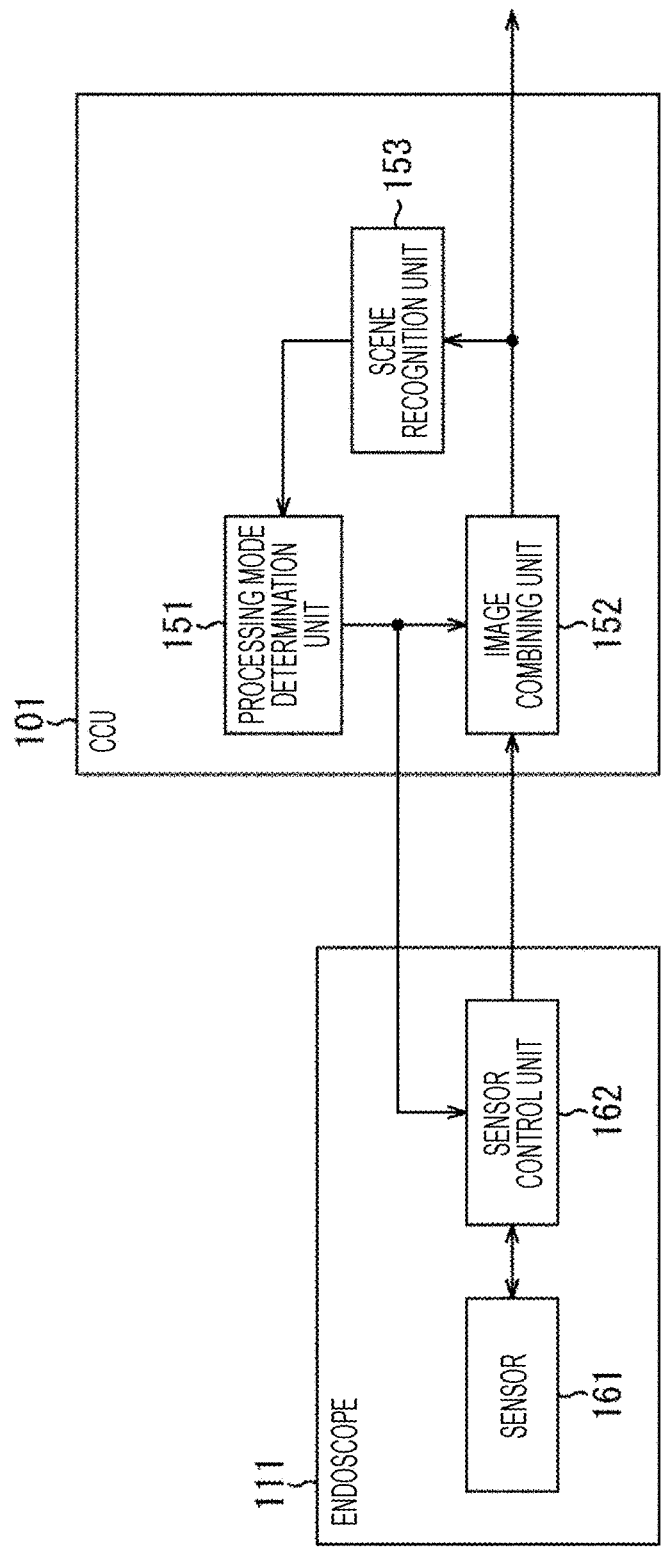
FIG. 10 is a diagram illustrating a detailed exemplary configuration of a CCU and an endoscope according to a second embodiment.

FIG. 10 is a diagram illustrating a detailed exemplary configuration of the CCU 101 and the endoscope 111 according to the second embodiment. Note that in the CCU 101 and the endoscope 111 in FIG. 10, the same reference numerals are given to the blocks corresponding to the CCU 101 and the endoscope 111 in FIG. 2, and repetitive description thereof will be omitted as appropriate.

Specifically, the CCU 101 in FIG. 10 is different from the CCU 101 in FIG. 2 in that a scene recognition unit 153 is provided at a stage following the image combining unit 152, and that a scene recognition result obtained by the scene recognition unit 153 is fed back to the processing mode determination unit 151. Note that the endoscope 111 in FIG. 10 and the endoscope 111 in FIG. 2 have a same configuration.

In the CCU 101 of FIG. 10, an output image (image signal) output from the image combining unit 152 is input to the scene recognition unit 153. The scene recognition unit 153 performs scene recognition processing on the output image (intraoperative image) from the image combining unit 152. By the scene recognition processing, a predetermined scene is recognized from the output image (intraoperative image), and the surgical scene is automatically discriminated. Subsequently, a scene recognition result (surgical scene discrimination result) obtained in the scene recognition processing is fed back to the processing mode determination unit 151.

Note that, for example, the scene recognition result (surgical scene discrimination result) fed back from the scene recognition unit 153 to the processing mode determination unit 151 can include the following information.

That is, for example, it is possible to include a surgical scene discrimination result as being narrowband imaging (NBI), fluorescence observation, or normal observation, corresponding to distribution analysis of RGB histograms on an output image (intraoperative image).

Moreover, for example, it is possible to include a surgical scene discrimination result as being a suture corresponding to detection of a thread or a suture needle included in an output image (intraoperative image).

Furthermore, it is possible to include, for example, a surgical scene discrimination result as being a scope movement corresponding to detection of a frame difference or motion vector of an output image (intraoperative image). Moreover, for example, it is possible to include a surgical scene discrimination result as being stripping (normal stripping or careful stripping) corresponding to detection of the forceps 135 included in the output image (intraoperative image) and motion detection of the forceps 135.

Note that the surgical scene discrimination results listed herein are illustrative, and for example, it is allowable to cause another scene recognition result obtained using known image analysis processing to be fed back to the processing mode determination unit 151.

The scene recognition result (discrimination result of the surgical scene) corresponding to the output image (intraoperative image) is input from the scene recognition unit 153 to the processing mode determination unit 151 at a predetermined timing.

In a case where the scene recognition result has been input from the scene recognition unit 153, the processing mode determination unit 151 determines the processing mode corresponding to a surgical scene specified by the scene recognition result (surgical scene discrimination result) with reference to the correspondence table stored beforehand (for example, the correspondence table in FIG. 4 or FIG. 6). The processing mode determination unit 151 supplies the determined processing mode to the image combining unit 152 and to the sensor control unit 162 of the endoscope 111.

The sensor control unit 162 controls the sensor 161 on the basis of the processing mode supplied from the processing mode determination unit 151. Moreover, on the basis of the processing mode supplied from the processing mode determination unit 151, the image combining unit 152 performs predetermined image processing on an image signal supplied from the endoscope 111 (the sensor control unit 162 thereof) via a camera cable.

(Image Combining Processing Flow)

Figure 11:
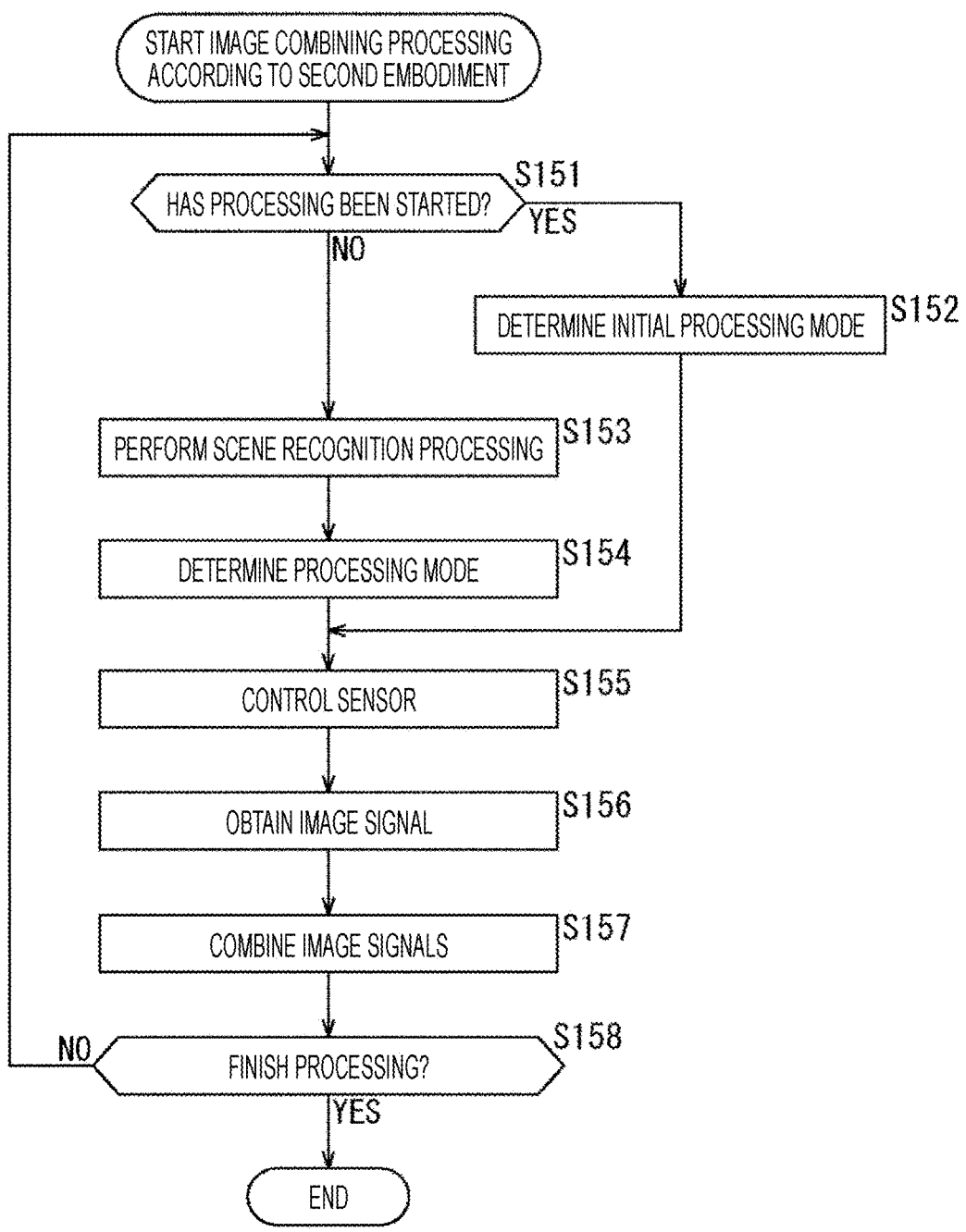
FIG. 11 is a flowchart illustrating an image combining processing flow according to the second embodiment.

Next, an image combining processing flow according to the second embodiment will be described with reference to the flowchart in FIG. 11.

In step S151, it is determined whether processing of the endoscopic surgery system 10 has been started. In a case where it is determined in step S151 that the processing has been started, the processing proceeds to step S152.

In step S152, the processing mode determination unit 151 determines an initial processing mode, and supplies the determined initial processing mode to the image combining unit 152 and the sensor control unit 162.

That is, for example, the initial processing mode set beforehand is to be determined because the scene recognition unit 153 cannot obtain an output image (intraoperative image) from the image combining unit 152 immediately after the processing is started in the endoscopic surgery system 10 (the CCU 101 thereof), and that the scene recognition result (surgical scene discrimination result) cannot be fed back to the processing mode determination unit 151.

In another case where it is determined in step S151 that the processing has not been started, the processing proceeds to step S153. In step S153, the scene recognition unit 153 performs scene recognition processing on an output image (intraoperative image) corresponding to an image signal from the image combining unit 152.

With this processing in step S153, a predetermined scene from the output image (intraoperative image) is recognized and the surgical scene is automatically discriminated. Subsequently, the scene recognition result (surgical scene discrimination result) obtained in the processing of step S153 is fed back to the processing mode determination unit 151.

In step S154, the processing mode determination unit 151 determines a processing mode corresponding to the surgical scene specified by the scene recognition result (surgical scene discrimination result) obtained in the processing of step S153, with reference to the correspondence table stored beforehand.

For example, in a case where the single-chip sensor 161-1 is applied in the imaging system of the endoscope 111, the processing mode determination unit 151 determines the processing mode corresponding to the surgical scene discrimination result obtained as a feedback, with reference to the correspondence table in FIG. 4. Moreover, for example, in a case where the three-chip sensor 161-3 is applied in the imaging system of the endoscope 111, the processing mode determination unit 151 determines the processing mode corresponding to the surgical scene discrimination result obtained as a feedback, with reference to the correspondence table in FIG. 6.

Figure 9:
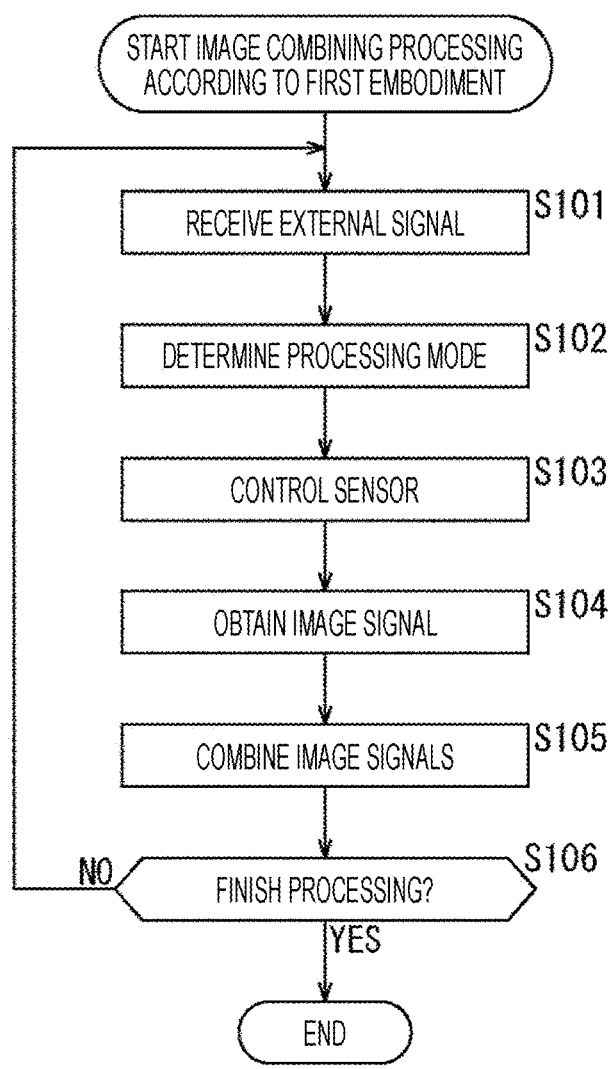
FIG. 9 is a flowchart illustrating an image combining processing flow according to the first embodiment.

In steps S155 to S157, the sensor control unit 162 controls the sensor 161 on the basis of the processing mode determined by the processing in step S154, similarly to the steps S103 to S105 of FIG. 9, and the image signals are combined (processed) by the image combining unit 152 on the basis of the processing mode determined by the processing in step S154. The output image obtained in the processing of step S157 is output at a predetermined frame rate.

In step S158, it is determined whether to finish the processing. In a case where it is determined in step S158 that the processing is not to be finished, the processing returns to step S151 to repeat the subsequent processing. In addition, in a case where it is determined in step S158 that the processing is to be finished, the image combining processing of the second embodiment in FIG. 11 is finished.

The image combining processing flow according to the second embodiment has been described above. In this image combining processing, the processing mode determination unit 151 refers to the correspondence table (for example, the correspondence table in FIG. 4 or FIG. 6) to determine the processing mode corresponding to the surgical scene specified by the scene recognition result (surgical scene discrimination result), and then, the sensor control unit 162 and the image combining unit 152 perform processing corresponding to the processing mode determined by the processing mode determination unit 151. That is, an appropriate processing mode corresponding to the surgical scene is determined by the correspondence table (for example, the correspondence table in FIG. 4 or FIG. 6) and the processing corresponding to the processing mode is performed, making it possible to provide an optimal video image to the operator in accordance with the surgical scenes.

4. Modification (Determination of Processing Mode by Planning)

While the above description is a case where the processing mode is determined in accordance with the external signal or the surgical scene specified by the scene recognition, the processing mode determination method may include, for example, a method of determining an appropriate processing mode in accordance with a surgery plan created beforehand. Specifically, for example, it is allowable to perform preliminary planning of the details of a surgery using a three-dimensional model to associate each of surgical sites (affected sites) with a processing mode (for example, associating the high definition mode with a treatment for a certain affected site). Under this planning, in a case where future implementation of the treatment for the target surgical site (affected site) is detected from an output image (intraoperative image), it is sufficient to shift to the processing mode associated with the surgical site (affected site).

5. Configuration of Computer

A series of processing (for example, image combining processing) described above can be executed in hardware or with software. In a case where the series of processing is executed with software, a program included in the software is installed in a computer. Herein, the computer includes, for example, a computer incorporated in a dedicated hardware, and a general-purpose personal computer on which various types of functions can be executed.

FIG. 12 is a block diagram illustrating an exemplary configuration of hardware of a computer on which the series of processing described above is executed by a program.

In a computer 200, a central processing unit (CPU) 201, a read only memory (ROM) 202, a random access memory (RAM) 203 are interconnected with each other via a bus 204. The bus 204 is further connected with an input/output interface 205. The input/output interface 205 is connected with an input unit 206, an output unit 207, a recording unit 208, a communication unit 209, and a drive 210.

The input unit 206 includes a key board, a mouse, a microphone, and the like. The output unit 207 includes a display, a speaker, and the like. The recording unit 208 includes hardware, a non-volatile memory, and the like. The communication unit 209 includes a network interface and the like. The drive 210 drives a removable medium 211 including a magnetic disk, an optical disk, a magneto-optical disk, a semiconductor memory, or the like.

On the computer 200 configured as above, the series of above-described processing is executed by operation such that the CPU 201 loads, for example, a program stored in the recording unit 208 onto the RAM 203 via the input/output interface 205 and the bus 204 and executes the program.

The program executed by the computer 200 (CPU 201) can be recorded, for example, in the removable medium 211 such as a package medium and be provided. Alternatively, the program can be provided via a wired or wireless transmission medium including a local area network, an Internet, and digital satellite broadcasting.

On the computer 200, the program can be installed in the recording unit 208 via the input/output interface 205, by attaching the removable medium 211 to the drive 210. In addition, the program can be received at the communication unit 209 via a wired or wireless transmission medium and be installed in the recording unit 208. Alternatively, the program can be installed in the ROM 202 or the recording unit 208 beforehand.

Note that the program executed by the computer 200 may be a program processed in a time series in an order described in the present description, or can be a program processed in parallel or in a required timing such as being called.

Note that in the present description, processing steps describing a program required for causing the computer 200 to execute various types of processing are not necessarily processed in sequentially in an order described in the flowchart. The processing steps may include steps executed in parallel or individually (for example, parallel processing or processing by objects).

In addition, the program can be processed by one computer or can be handled with distributed processing by a plurality of computers. Furthermore, the program can be transferred to a remote computer and be executed.

Furthermore, in the present description, the system represents a set of multiple constituents (devices, modules (parts), or the like). In other words, all the constituents may be in a same housing but they do not have to be in the same housing. Accordingly, a plurality of apparatuses, housed in separate housings, connected via a network can be a system. An apparatus in which a plurality of modules is housed in one housing can also be a system.

Note that embodiments of the present technology are not limited to the above-described embodiments but can be modified in a variety of ways within a scope of the present technology. For example, the present technology can be configured as a form of cloud computing in which one function is shared in cooperation for processing among a plurality of devices via a network.

Moreover, each of steps described in the above flowcharts can be executed on one apparatus or shared by a plurality of apparatuses for processing. Furthermore, in a case where one step includes a plurality of stages of processing, the plurality of stages of processing included in the one step can be executed on one apparatus or can be shared by a plurality of apparatuses.

Note that the present technology can be configured as follows.

(1) An information processing apparatus including:
a processing mode determination unit that determines, in accordance with surgical scenes, a processing mode for an in-vivo image captured by an imaging apparatus including an imaging element arranged so as to enable pixel shift processing; and
a processing unit that processes an image output from the imaging apparatus, in accordance with the processing mode.

(2) The information processing apparatus according to (1),
in which the imaging apparatus includes a control unit that controls the imaging element in accordance with the processing mode, and
the processing mode determination unit supplies the processing mode to the control unit.

(3) The information processing apparatus according to (1) or (2),
in which the processing mode includes a mode capable of providing, by the pixel shift processing, a high definition image having higher definition than in the in-vivo image captured by the imaging element.

(4) The information processing apparatus according to (3),
in which the processing mode further includes at least one of a mode capable of providing an image with less noise than in the in-vivo image captured by the imaging element and a mode capable of providing an image in which motion appears smoother than in the in-vivo image captured by the imaging element.

(5) The information processing apparatus according to any one of (1) to (3),
in which the imaging apparatus includes at least three imaging elements.

(6) The information processing apparatus according to any one of (1) to (5), in which the mode determination unit determines the processing mode in accordance with an external signal input from an outside.

(7) The information processing apparatus according to (6), in which the mode determination unit determines the processing mode in accordance with operation performed by the operator to switch the processing mode.

(8) The information processing apparatus according to (6), in which the mode determination unit determines the processing mode in accordance with a signal indicating power on-off of a treatment tool, output from a treatment tool apparatus.

(9) The information processing apparatus according to (6), in which the mode determination unit determines the processing mode in accordance with a light source switching signal output from a light source apparatus.

(10) The information processing apparatus according to (1), in which the mode determination unit determines the processing mode in accordance with a surgery plan created beforehand.

(11) The information processing apparatus according to (10), in which the mode determination unit determines the processing mode in accordance with the processing mode for each of surgical sites planned beforehand in the surgery plan.

(12) The information processing apparatus according to any one of (1) to (5), further including a scene recognition unit that recognizes a predetermined scene on the basis of the image output from the imaging apparatus, in which the mode determination unit determines the processing mode on the basis of a recognition result obtained by the scene recognition unit.

(13) The information processing apparatus according to (4), in which the imaging apparatus includes a control unit that controls the imaging element in accordance with the processing mode, the processing mode includes:

a first mode in which pixel shift processing is not performed and the in-vivo image captured by the imaging element is output at a constant frame rate;

a second mode in which pixel shift processing is performed and an image obtained by the pixel shift processing and having higher definition than in the in-vivo image captured by the imaging element is output at a frame rate same as a frame rate in the first mode;

a third mode in which pixel shift processing is not performed and an image obtained by a plurality of shots of imaging within a predetermined time is output at a frame rate higher than in the first mode; and a fourth mode in which pixel shift processing is not performed and images obtained by a plurality of shots of imaging within a predetermined time are added and then output at a frame rate same as the frame rate in the first mode, and a surgical scene suitable for providing one of an image having higher definition than in the in-vivo image captured by the imaging element and an image with less noise than in the in-vivo image captured by the imaging element is associated with one of the second mode and the fourth mode, and a surgical scene suitable for providing an image in which motion appears smoother than in the in-vivo image captured by the imaging element is associated with the third mode.

(14) The information processing apparatus according to (4), in which the imaging apparatus includes at least three imaging elements, the processing mode includes:

a first mode in which each of RGB planes is imaged at a same timing and an image obtained by RGB plane images and having higher definition than in the in-vivo image captured by the imaging element is output at a constant frame rate; and a second mode in which each of the RGB planes is imaged at different timings and an image obtained by combining RBG plane images having close imaging times among the RBG plane images captured with shifted imaging timings is output at a higher frame rate than in the first mode, and a surgical scene suitable for providing an image having higher definition than in the in-vivo image captured by the imaging element is associated with the first mode, and a surgical scene suitable for providing an image in which motion appears smoother than in the in-vivo image captured by the imaging element is associated with the second mode.

(15) The information processing apparatus according to any one of (1) to (14), in which the processing mode determination unit stores a table associating the surgical scene with the processing mode, and determines the processing mode with reference to the table.

(16) The information processing apparatus according to (3), in which the high definition image is an image having a horizontal resolution of 3840 or more.

(17) An information processing method of an information processing apparatus, the method including steps of:

determining, by the information processing apparatus in accordance with surgical scenes, a processing mode for an in-vivo image captured by an imaging apparatus including an imaging element arranged so as to enable pixel shift processing; and processing an image output from the imaging apparatus, by the information processing apparatus in accordance with the processing mode.

(18) An endoscope system including an endoscope and an information processing apparatus, in which the endoscope includes:

an imaging element arranged so as to enable pixel shift processing; and a control unit that controls the imaging element, the information processing apparatus includes:

a processing mode determination unit that determines a processing mode for an in-vivo image captured by the endoscope, in accordance with surgical scenes; and a processing unit that processes an image output from the endoscope, in accordance with the processing mode, and the control unit controls the imaging element in accordance with the processing mode.

REFERENCE SIGNS LIST

10 Endoscopic surgery system
101 CCU
102 Light source apparatus
103 Treatment tool apparatus
104 Pneumoperitoneum apparatus
105 Display apparatus 106 Recorder
107 Printer
111 Endoscope
112 Energy treatment tool
121 Foot switch
131 to 134 Trocar
135 Forceps
151 Processing mode determination unit
152 Image combining unit
153 Scene recognition unit
161 Sensor
161-1 Single-chip sensor
161-3 Three-chip sensor
162 Sensor control unit
181-R, 181-G, 181-B Buffer
182 Misalignment detection unit
183 Misalignment correction unit
200 Computer
201 CPU

The invention claimed is:

1. A medical information processing system, comprising:
processing circuitry configured to:
switch a processing mode based on a switching signal coupled to a light source configured to output a first light for narrow band imaging or fluorescence image or a second light for normal imaging to a medical imaging device, the switching signal indicating which of the first light and the second light is output from the light source,
output, in a first processing mode when the first light is output from the light source, a first resolution image generated by combining a plurality of medical images generated by the medical imaging device,
output, in a second processing mode when the second light is output from the light source, a second resolution image, the first resolution image having a higher resolution than the second resolution image.

2. The medical information processing system according to claim 1, wherein the switching signal is generated based on a manual operation by a doctor.

3. The medical information processing system according to claim 1, wherein the first resolution image is an image having a horizontal resolution of 3840 pixels or more.

4. The medical information processing system according to claim 1, wherein the combining of the plurality of the medical images is done by a pixel shift processing.

5. The medical information processing system according to claim 1, wherein
the medical imaging device includes control circuitry configured to control an imaging element in accordance with the processing mode, and
the processing circuitry is configured to supply information regarding the processing mode to the control circuitry.

6. The medical information processing system according to claim 1, wherein the first resolution image has higher definition than in the plurality of medical images.

7. The medical information processing system according to claim L wherein the medical imaging device includes at least three imaging elements.

8. The medical information processing system according to claim 7, wherein the three imaging elements are a red sensor, a green sensor and a blue sensor.

9. The medical information processing system according to claim 1, wherein the medical imaging device include a single-chip imaging element.

10. The medical information processing system according to claim 1, wherein the processing circuitry is configured to further determine the processing mode in accordance with a signal indicating power on-off of a treatment tool, output from the treatment tool.

11. The medical information processing system according to claim 1, wherein the first resolution image is a 4K image and the second resolution image is a HD (High Definition) image.

12. An endoscope system, comprising;
an endoscope; and
an information processing apparatus, wherein
the endoscope includes:
an imaging element, and
control circuitry configured to control the imaging element, the information processing apparatus includes:
processing circuitry configured to:
switch a processing mode based on a switching signal coupled to a light source configured to output a first light for narrow band imaging or fluorescence image or a second light for normal imaging to a medical imaging device, the switching signal indicating which of the first light and the second light is output from the light source,
output, in a first processing mode when the first light is output from the light source, a first resolution image generated by combining a plurality of medical images generated by the medical imaging device,
output, in a second processing mode when the second light is output from the light source, a second resolution image, the first resolution image having a higher resolution than the second resolution image.

13. An information processing method of an information processing apparatus, the method comprising:
switching, using processing circuitry, a processing mode based a switching signal coupled to a light source configured to output a first light for narrow band imaging or fluorescence image or a second light for normal imaging to an imaging device, the switching signal indicating which of the first light and the second light is output from the light source,
outputting, in a first processing mode, when the first light is output from the light source, a first resolution image generated by combining a plurality of images generated by the imaging device,
outputting, in a second processing mode when the second light is output from the light source, a second resolution image, the first resolution image having a higher resolution than the second resolution image.

* * * * *